United States Patent [19]

Aramaki

[11] Patent Number: 4,686,846

[45] Date of Patent: Aug. 18, 1987

[54] AIR/FUEL RATIO MEASURING DEVICE

[75] Inventor: Yuichiro Aramaki, Tokyo, Japan

[73] Assignee: Kabushiki Kaisha Tsukasa Sokken, Tokyo, Japan

[21] Appl. No.: 802,458

[22] Filed: Nov. 27, 1985

[51] Int. Cl.⁴ .................... G01N 27/12; G01M 15/00
[52] U.S. Cl. ........................................... 73/23; 73/116
[58] Field of Search ................... 73/23, 116; 436/143;
422/83, 98; 204/18, 409; 123/440, 489; 60/276

[56]  References Cited
U.S. PATENT DOCUMENTS 4,555,931 12/1985 Amimoto et al. ...................... 73/23

Primary Examiner—Stewart J. Levy
Assistant Examiner—Joseph W. Roskos
Attorney, Agent, or Firm—Parkhurst & Oliff

[57]  ABSTRACT

An air-fuel ratio measuring device in which an exhaust gas suction pipe with a throttle nozzle and a dilution air pipe are joined with each other at a surge tank to which a suction pump is connected and two capillary tubes are branched from the two pipes on the upstream side of the surge tank, respectively. Further, a mixture pipe is extended from a joining point of the two capillary tubes. This device is simple in structure and makes it possible to accurately measure the air-fuel ratio.

4 Claims, 3 Drawing Figures

AIR/FUEL RATIO MEASURING DEVICE

BACKGROUND OF THE INVENTION

This invention relates to a device for measuring air-fuel ratio of combustion engines.

In various industrial fields, there have been used engines which generate combustion energy by burning air with alcoholic fuel such as methanol and ethanol, or hydrocarbon fuel such as gasoline, gas oil and propane. Among other applications, internal combustion engines have been widely used in automobiles.

For design, manufacture and maintenance of these internal combustion engines, it is important that the ratio of an amount of air to that of fuel consumed in an engine (the ratio is normally defined as mass ratio and is called air-fuel ratio hereinafter) is measured to increase engine efficiency and to prevent environmental pollution.

In conventional methods for measuring the air-fuel ratio, there have been used, in recent years, a residual oxygen density measuring method and a residual carbon dioxide density measuring method in both of which an amount of exhaust gas is sampled to measure the density of residual oxygen and carbon dioxide therein, respectively. In these methods, it is desirable that accurate air-fuel ratio can be obtained, these measuring principles are easily understandable, these measuring mechanisms are simple, the ratio can be measured for a short time and these measuring operations are convenient.

In an air-fuel ratio measuring device for carrying out the above methods, an amount of exhaust gas is sampled and completely oxidized through a catalyst member for oxidation and thereafter the density of residual oxygen is measured. Thus, the air-fuel ratio can be measured irrespective of the amount of sampled exhaust gas. Instead of the density of residual oxygen, the density of residual carbon dioxide may be measured to obtain the air-fuel ratio.

Functional expressions for obtaining the air-fuel ratio by the above residual oxygen density measuring methods are illustrated by the following expressions (1) to (3). The expression (3) must be slightly amended in the case of the residual dioxide carbon density measuring method.

Calculation Expressions:

$$AFR = \lambda \cdot AFRstoic \tag{1}$$

$$AFRstoic = \frac{34.505(4 + n - 2y)}{12.011 + 1.008n + 16y} \tag{2}$$

$$\lambda = 1 + \frac{C}{0.209 - C}\left(1 + \frac{0.209(n + 2y)}{4 + n - y}\right) \tag{3}$$

wherein,
AFR: air-fuel ratio (mass ratio)
AFRstoic: stoichiometric air-fuel ratio
$\lambda$: equivalence ratio
n: H/C ratio (number of hydrogen atoms per carbon atom in fuel)
y: O/C ratio (number of oxygen atoms per carbon atom in fuel)
C: density of residual oxygen Residual oxygen always exists when air is supplied to a combustion engine in more than a theoretically necessary amount for complete combustion (this condition is called lean burn region). In this case, the measurement of the residual oxygen density is possible. However, residual oxygen does not exist when air is supplied to a combustion engine in a theoretically necessary amount for complete combustion (this is called theoretical ratio) or less than that (this condition is called rich burn region). In these cases, the measurement of the residual oxygen is impossible.

To solve the above problem in the rich burn region, an amount of exhaust gas to be sampled is diluted with a predetermined amount of air. A calculation expression in this case is as follows.

$$\lambda = 1 + \frac{C - Z}{0.209 - C}\left(1 + \frac{0.209(n + 2y)}{4 + n - 2y}\right) \tag{4}$$

wherein Z is air dilution ratio.

Internal combustion engines are often operated in the rich burn region. Therefore, dilution mechanisms for diluting sampled exhaust gas with air are very important to measure accurately the air-fuel ratio.

There have been two typical air dilution mechanisms.

The first conventional air dilution mechanism has an exhaust gas suction line for sucking exhaust gas and an air suction line disposed in parallel with the exhaust gas suction line in order to suck air for dilution from a high pressure air source. The exhaust gas suction line and air suction line are connected to each other at a junction point from which a mixture line for transmitting a mixture fluid of the exhaust gas and the dilution is extended. On the exhaust gas suction line are provided a suction pump and a pressure adjustment valve with a servo-mechanism. On the air suction line are provided a motor drive valve and a pressure adjustment valve with a servo-mechanism, and on the mixture line are provided a catalyst member, an oxygen density sensor, a pressure adjustment valve with a servo-mechanism and an exhaust pump.

The above lines having an air dilution mechanism are provided with pressure adjustment valves with servo-mechanisms. Accordingly, the air-fuel ratio can be measured steadily even if the pressure of the exhaust gas and the dilution air changes in a wide region. However, the pressure adjustment valves are not only expensive but also complicated in construction.

In contrast, the second conventional air dilution mechanism has a plurality of capillary tubes on an exhaust gas suction line and an air suction line, respectively, and a mixture line is extended from a junction point of the two lines. The mixture line has a catalyst member, an oxygen density sensor and an exhaust pump. The capillary tubes are so designed that their Reynolds number is very low. The second mechanism is relatively inexpensive and easily maintained. However, the air dilution ratio cannot be consistently calculated if the pressure of the sampled exhaust gas changes and if the viscosity of the exhaust gas changes due to the change of its temperature.

Further, in combination engines, there often occur pulsations with a large amplitude and a short cycle. In such cases, even the first mechanism is not useful because the pressure adjustment valves with servo-mechanisms cannot overcome such pulsations.

SUMMARY OF THE INVENTION

It is an object of this invention to provide an air-fuel rato measuring device which is relatively inexpensive, which can stabilize the flow ratio of exhaust gas and dilution air and which can measure the air-fuel ratio accurately even if pulsations exist in the exhaust gas.

According to this invention, there is provided an air-fuel ratio measuring device for measuring the air-fuel ratio in such a manner to measure a residual component after air for dilution and sampled exhaust gas are mixed with each other, which comprises: an exhaust gas suction line for sucking the exhaust gas; a dilution air suction line for sucking the dilution air, joined with the exhaust gas suction line; two capillary tubes branched from the exhaust gas suction line and the dilution air suction line on the upstream side of a joining position of the two lines; a mixture line extending from a joining point of the two capillary tubes and having members for measuring the residual component; and a throttle nozzle provided on the exhaust gas suction line on the upstream-side of a branch point of the capillary tube.

The characteristic features and advantageous effects will be clarified with reference to the following drawings.

DETAILED DESCRIPTION OF THE INVENTION

First, as conducive to a full understanding of the nature and utility of the present invention, a brief consideration of the above first and second dilution mechanisms will be presented below with reference to FIGS. 2 and 3.

Figure 2:
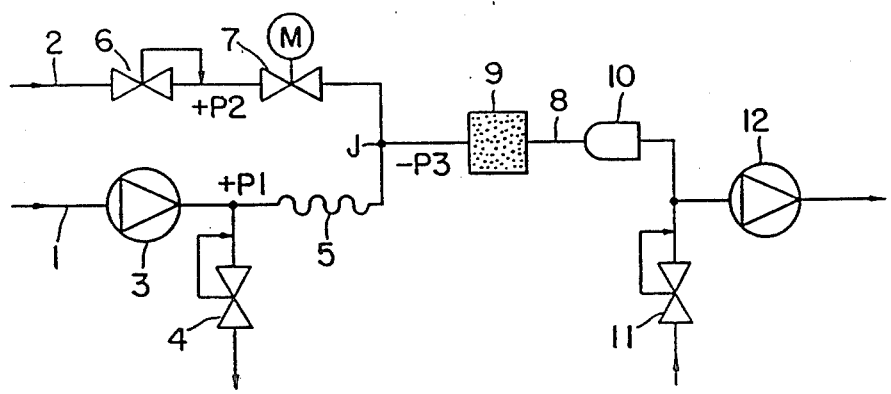
FIG. 2 is a view showing a first conventional air-fuel ratio measuring device.

The first conventional device, as shown in FIG. 2, has an exhaust gas suction line 1 and a dilution air suction line 2. The exhaust gas suction line 1 is provided with a suction pump 3 for sucking exhaust gas, a pressure stabilization (adjustment) valve 4 with a servo-mechanism and capillary tube 5, and the pressure of the exhaust gas is kept at a constant value $+P_1$ on the discharging side of the pump 3. The dilution air suction line 2 is provided with a pressure stabilization valve 6 with a servo-mechanism and a motor drive valve 7 and air pressure on the downstream side of the valve 6 is kept at a constant value $+P_2$. A mixture line 8 is connected to the above two lines at the joining point J thereof and is provided with a catalyst member 9, an oxygen density sensor 10 and an exhaust pump 12. The pressure of the line 8, the catalyst member 9 and the sensor 10, is kept by a pressure stabilization valve 11 with a servo-mechanism at a constant value $-P_3$.

Further, in this device, the exhaust gas is sucked by the pump 3 through the exhaust gas suction line 1, the pressure on the discharging side of the pump 3 is kept by the valve 4 at a constant value $+P_1$ and the excessive sample gas is discharged through the valve 4. The sample gas passes through the capillary tube 5 and flows into the mixture line 8 at the joining point J.

Dilution air is supplied from the high pressure source through the valve 6 and the pressure on the downstream side of the valve 6 is kept at a constant value $+P_2$. The dilution air flows into the line 8 through the motor drive valve 7.

The sample gas and dilution air join at the joining point J and are oxidized completely. The residual oxygen density is measured by a known oxygen density sensor 10. The gas having passed through the sensor 10 is discharged by the pump 12. Thus, the ratio of air to sample gas is kept constant due to the stabilized pressure $+P_1$, $+P_2$ and $-P_3$.

Figure 3:
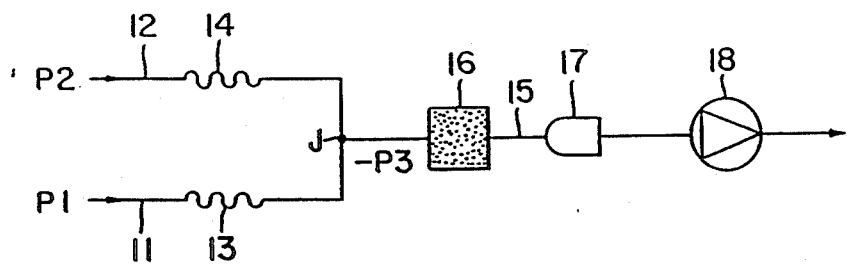
FIG. 3 is a view showing a second conventional air-fuel ratio measuring device.

The second conventional device has, as shown in FIG. 3, an exhaust gas suction line 11 with a capillary tube 13 and a dilution air suction line 12 with a capillary tube 14. Sample gas flows into a mixture line 15 through the capillary tube 13 and the joining point J while the dilution air sucked from the atmospheric environment flows into the line 15 through the capillary tube 14. The line 15 has a catalyst member 16, an oxygen density sensor 17 and a pump 18 in the same manner as that of the first device. The Reynolds number of the two capillary tubes 13 and 14 is sufficiently low and the air dilution ratio is kept constant irrespective of the change of negative pressure $-P$ when an input pressure $P_1$ of the sample gas is equal to an atmospheric pressure $P_2$.

The first device is expensive, as a whole, because of expensive pressure stabilization valves and is complicated in structure. The second device is not so expensive and is simple in structure. However, in the second device, the air-fuel ratio cannot be measured accurately when the pressure of the exhaust gas changes.

To solve these problems, there is provided an air-fuel ratio measuring device according to this invention mentioned below.

Figure 1:
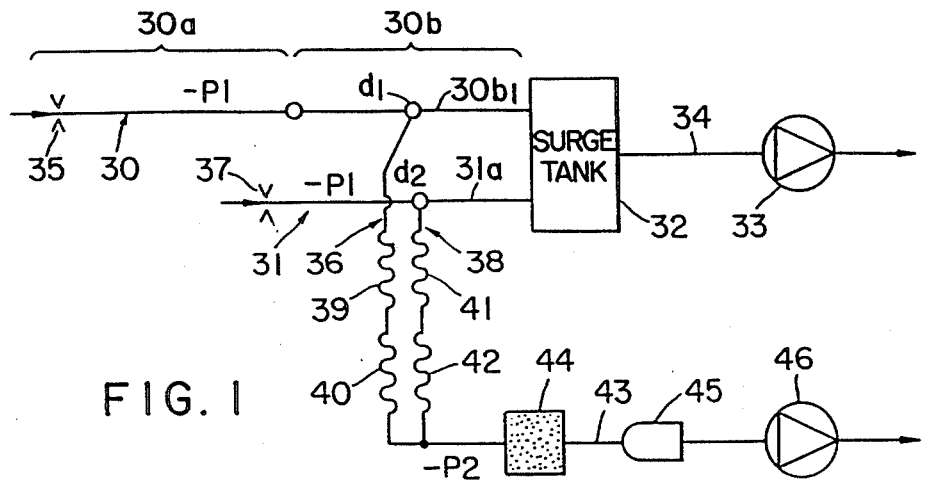
FIG. 1 is a view showing a construction of an air-fuel ratio measuring device according to this invention.

In FIG. 1, an exhaust gas suction pipe 30 for sucking exhaust gas and a dilution air suction pipe 31 for sucking air from the atmospheric environment in order to dilute the exhaust gas therewith are connected to a surge tank 32 in parallel with each other. A suction pump 33 is connected to the surge tank through a pipe 34. On the left side as viewed in FIG. 1 (upstream side) is formed a throttle nozzle 35, on the downstream side of which a pipe portion 30a has a predetermined extension. To the pipe portion 30a is connected a pipe portion 30b whose intermediate portion has a branch point $d_1$ from which an exhaust gas capillary tube 36 is extended. Further, at the left end of the dilution air suction pipe 31 as viewed in FIG. 1 (upstream side) is formed a throttle nozzle 37 and the pipe 31 has, at its center, a branch point $d_2$ from which a dilution air capillary tube 38 is extended.

The two capillary tubes 36, 38 each have two respective capillary tubes 39, 40 and 41, 42 (39, 41 are supplementary capillary tubes; 40, 42 are main capillary tubes) which join with each other and are connected to a mixture fluid pipe 43 having a catalyst member 44, an oxygen density sensor 45 and a suction pump 46.

The throttle nozzle 35 of the exhaust gas suction pipe 30 and the pipe portion 30a extending therefrom form a mechanism for absorbing pulsations. Sample gas of the exhaust gas is sucked by the pump 33 and the pressure of interior of the exhaust gas suction pipe 30 is kept at a negative value $-P_1$ (atmospheric pressure is defined as a datum pressure). The inner diameter of the pipe 30 is made to be sufficiently large as compared with the quantity of flow and most of pressure loss is caused by the throttle nozzle 35. The shape of throttle nozzle 35 and the pressure $-P_1$ are selected in a manner that the nozzle 35 always functions as a "sonic velocity nozzle" (the flow velocity of the exhaust gas at the throat of the nozzle is equal to a sonic velocity). The pulsating wave normally has a large amplitude. In this case, the pressure loss of the throttle nozzle 35 may reach an extremely large positive instantaneous value which is larger than the pressure $-P_1$ (ten times as much as the pressure $P_1$). However, it never decreases to a value of 0.7 times as much as the pressure $-P_1$.

The characteristic feature of the throttle nozzle 35 (sonic velocity nozzle) resides in that the volume flow of the gas passing through the nozzle on the upstream side of the nozzle is in proportion to only a sonic velocity, in other words, only the square root of absolute temperature of the gas. Accordingly, when the change of the temperature of the sample gas is not so large as compared with its absolute temperature and the change of the pressure on the downstream side of the nozzle is sufficiently small as compared with its absolute pressure, the volume flow on the downstream of the nozzle 35 is in proportion to the absolute value of the pressure of the sample gas flowing into the nozzle (the mass flow of the nozzle is in proportion to the absolute pressure of the sample gas and the sample gas expands on its downstream side under a substantially constant pressure). In this case, the throttle nozzle 35 is comparable to a resistance element r1 in an equivalent circuit concerning acoustical vibration engineering. Hereupon, a P→V and Q→I correspondence system is used. In this system, pressure is selected as a variable for indicating strength and flow volume is selected as a variable for indicating quantity.

Considering the P→V and Q→I correspondence system, an electric circuit theory is used for analyzing mechanical or fluid vibration in the field of acoustic vibration engeering. In this case, the variable for indicating strength is compared to voltage while the variable for indicating quantity is compared to electric current. When these conversions are carried out, the physical characteristics in mechanical and fluid vibration systems can be analyzed by substantially comparing the characteristics to that of concentrated constant system or distributed constant system including resistance, condenser or inductance in an electric system. In the correspondence conversion of P-Q system, each element is defined in the following manner.

Resistance $r = \delta P/q$, unit $Pa \cdot S/m^3$

Compliance $C = V_o/(P_o \cdot Y)$, unit $m^3/Pa$

Inertance $1 = L \cdot /3 p/S$, unit $kg/m^4$ wherein:
$\delta P$: pressure difference
q: quantity of flow
$V_o$: inner volume of a surge tank
$P_o$: absolute pressure
Y: specific heat at constant pressure/specific heat at constant volume
L: length of pipe
$\rho$: density
S: sectional area of the pipe The pipe 30 is comparable to a pressure transmission line in the form of the distributed constant system having a mechanical transmission impedance Zt. Therefore, according to a simulation technique in acoustic vibration engineering, with respect to the change of the pressure and quantity of sample gas, the mechanism of this invention can be compared to a model of an equivalent circuit in which an electric current flows into a transmission line in the form of the distributed constant system through a resistance element r1 from an electric signal source.

According to an electric circuit theory, if the resistance element r1 is much larger than the impedance Zt ($r1 >> Zt$), the circuit forms a low-pass filter comprising the resistance element r1 and an equivalent condenser $C_1$ formed by the transmission line in the form of the distributed constant system (in the mechanism of the invention, the condenser $C_1$ corresponds to an equivalent mechanical compliance which is equal to a value obtained in a manner to multiply a compliance $C_2$ per unit length of the sample pipe by its whole length L). With respect to the frequency of the electric signal source (the frequency corresponds to that of pulsations on the inlet side of the sample pipe), waves having a frequency at or above a roll off frequency ($Fr = 1/(2\pi \cdot r1 \cdot C_1)$) decrease extremely in inverse proportion to their frequencies. Further, in this mechanism, an inherent resonance phenomenon having a high characteristic frequency in a distributed constant type transmission line (the resonance phenomenon corresponds to air resonance in a pipe in a distributed constant type pressure transmission line) can be almost neglected because its frequency component decreases remarkably. In this system, the condition at the other end of the distributed constant type transmission line also influences its characteristics. However, in this invention, the surge tank 32 having a large mechanical compliance $C_3$ is provided at a position corresponding to the end of the condensor (corresponding to the pipe 30) whereby the above advantageous effects are increased.

The above is an operational principle of the mechanism for absorbing pulsations in the embodiment of this invention, and further exemplary dimensions adopted for this invention and each calculated constant will be mentioned below.

Coefficient of the throttle nozzle 35—5 l/min/atm (inner diameter of the nozzle—0.9 mm)
Equivalent resistance r1—940×$10^6$ Pa·S/$m^2$
Suction negative pressure $-P_1$—26 KPa (−200 torr)
Sizes of exhaust gas suction pipe when its inner diameter is 4.3 mm and its length is 3 m:
  Mechanical transmission impedance—24×$10^6$ Pa·S/$m^3$
  Equivalent mechanical compliance $C_1$—400×$10^{-12}$ $m^3$/Pa
  Roll off frequency Fr—0.4 Hz
Sizes of exhaust gas suction pipe when its inner diameter is 2.7 mm and its length is 3 m:
  Mechanical transmission impedance Zt—60×$10^6$ Pa·S/$m^3$
  Equivalent mechanical compliance $C_1$—160×$10^{-12}$ $m^3$/Pa
  Roll off frequency Fr—1.0 Hz
  Volume of the surge tank—250 cc
  Equivalent compliance $C_3$—2.3×$10^{-9}$ $m^3$/Pa As shown in this embodiment, in this mechanism, the equivalent resistance y1 is determined to be much larger than the mechanical transmission impedance Zt(y1 >> Zt) and the roll off frequency Fr can be determined to be much lower than the frequency (flow velocity)/4L (length of pipe) (about 30 Hz when L is 3 m) at which a pipe resonance begins in the sample line as a distributed constant type pressure transmission line.

The pipe portion 30b, of the exhaust gas suction pipe 30, the surge tank 32 and the dilution air suction pipe 31 (including the throttle nozzle 37) form a pressure equalizing mechanism for equalizing the pressures of the respective branch points $d_1$, $d_2$ of the capillary tubes 36, 38 with each other.

The inner diameters of the pipes 30b, 31 are sufficiently large as compared with the flow rates in those pipes respectively, for example, the flow rates passing through the tubes 36, 38 are determined to be less than one fifth or one sixth of those flow rates passing through the pipes 30b, 31. Accordingly, the respective pressure losses of the interiors of the pipes 30b, 31 are minimal and the pressures of the interiors of the pipes 30b 31 become equal to the negative pressure $-P_1$. Like the nozzle 35, the shape and inner diameter of the nozzle 37 are so selected that the nozzle 37 functions as a "sonic velocity nozzle" (the flow velocity at the throat of the nozzle equals to a sonic velocity). Therefore, the pressures at the branch points $d_1$, $d_2$ forming the respective inlet portions of the two capillary tubes can be kept equal to each other without any pressure stabilization valve and servo-mechanism.

The joining point of the two capillary tubes 36, 38 has a negative pressure $-P_2$ and, therefore, the respective pressure losses of the capillary tubes 36, 38 are always kept equal to each other. As a result, the ratio of the flow rate of the sample gas flowing through the capillary tube 36 to that of the dilution air flowing through the capillary tube 38 is always kept constant.

There may be a case wherein the respective flow rates of the tubes 30b, 31 change due to the change of the suction pressure of the pump or the flow rate of the tube 30b changes due to the increase of mean pressure of the sample gas thereby to cause a slight pressure difference $\delta P_1$ between the two branch points $d_1$, $d_2$. However, the pressure difference $\delta P_1$ does not become a cause for changing the ratio of the two flow rates because the respective pressure losses $\delta P_2$ ($=P_2-P_1$) of the two tubes 36, 38 are sufficiently large (the ratio of $\delta P_1$ to $\delta P_2$ can be determined to be a value of one five or six hundreds).

In view of a function for preventing counter flow, the sample gas and the dilution air join at the surge tank 32 after passing through the pipe portions $30b_1$, $31a$ and there are pulsations in the tubes 30, 31 and the surge tank 32. The mixture gas in the tank 32 may flow toward the branch points $d_1$, $d_2$ and this counterflow is prevented by the tube portions $30b_1$, $31a$, of the pipes 30b, 31, located on the upstream side of the surge tank. That is, in this case, the analysis of the equivalent circuit is carried out in a manner that the pulsation signal source is compared to the surge tank 32. As mentioned above, the pipes correspond to these distributed constant type pressure transmission lines. The mechanism of this invention has the throttle nozzles 35, 37 at the side opposite to the pulsation signal source with respect to the pipes. The mechanical impedances of the two nozzles are compared to resistances, respectively, both of which are sufficiently larger than the respective mechanical impedances of the tubes. This system can be analyzed so as to be compared to an acoustic vibration system in which pulsations are generated at an open end on one side of a pipe with a closed end on the otherside thereof. That is, the movement of a wave surface moving backward due to a pulsating pressure of the interior of the surge tank 32 is very similar to that of a rigid piston whose front end surface corresponds to the wave surface. The piston is moved to a position at which the increase of the pressure of the interior of the pipe due to the decrease of the volume between the nozzle and the moving piston becomes equal to the magnitude of the pulsating pressure of the signal source. Thus, the maximum stroke of the piston is determined. The respective lengths of the pipe portions $30b_1$, $31a$ between the surge tank and the respective branch points $d_1$, $d_2$ is calculated to obtain their respective optimum values.

In addition, strictly speaking, the maximum stroke of the piston moving backward can be calculated in such a manner that the quantity of the moving velocity of the piston minus the flow velocity of the gas is integrated with respect to time because of the existence of steady flows of the tubes. However, in view of the frequency component of the pulsating pressure, the way of calculation is effective to know the most unsuitable value in design rather than the optimum value in design.

The capillary tubes 36, 38 will now be explained.

The temperature of the sample gas flowing into the capillary tube 36 from the branch point $d_1$ or the dilution air flowing into the capillary tube 38 from the branch point $d_2$, particularly, the temperature of the sample gas changes in a wide region according to the operating condition of an engine to be measured. As is known, the ratio of the flow rate of the dilution air to that of the flow rate of the sample gas cannot be steadily kept constant unless the temperature of the sample gas is equalized to that of the dilution air, even if the respective Reynolds numbers of the capillary tubes 36, 38 are low and, further, the pressure losses of the two capillary tubes 36, 38 are always equalized, because coefficient of viscosity of a gas varied with its temperature.

Therefore, in this invention, the two capillary tubes 36, 38 each have two supplementary capillary tubes 39, 41 and two main capillary tubes 40, 42 connected to the supplementary tubes 39, 41, respectively. The main capillary tubes 40, 41 have two inner diameters which are approximately one fifth or one sixth of those of the supplementary tubes 39, 41, respectively. The two supplementary tubes 39, 41 are mechanically congruous with each other and are in a state wherein the heat of the tubes 39, 41 can be transferred to each other. Likewise, the main capillary tubes 40, 42 are congruous with each other and are in a state wherein the heat of the tubes 40, 42 can be transferred to each other.

The operational principles of the above construction are as follows. That is, according to thermodynamics, the consistency of the temperature of a liquid passing through a tube with that of the wall of the tube due to heat transfer in the case of a streamline flow depends on the flow rate of the liquid and the length of the tube, but does not depend on the inner diameter of the tube. Furthermore, according to hydrodynamics, the pressure loss of a fluid passing through the tube in a streamline (laminar) flow region is in proportion to its flow rate and is in inverse proportion to the fourth power of the inner diameter of the tube.

Namely, the temperatures of sample gas and dilution air are equalized to each other in the respective capillary tubes 39, 41. The capillary tubes 39, 41 correspond to a preliminary thermal region where thermal distribution in the tube becomes stable before the sample gas and the dilution air flow into the main capillary tubes 40, 42, respectively. The difference between the pressure losses in the two capillary tubes 39, 41 due to the difference between the temperature of the sample gas in the capillary tube 39 and that of the dilution air in the capillary tube 41 can be neglected because the absolute value of the difference is remarkably small as compared with that of the difference between the pressure losses of the two main capillary tubes 40, 42.

In this manner, the temperature of the sample gas passing through the main capillary tube 40 is always equalized to that of the dilution air passing through the main capillary tube 42. In addition, if the pressure losses in the two tubes 40, 42 are equalized to each other, the ratio of the respective flow rates of the two tubes 40, 42 can be kept constant.

According to the above construction, the defects of a conventional air-fuel measuring device, that is the instability of the air dilution ratio due to the change of viscosity in response to the change of the temperature of the exhaust gas as well as the instability of the air dilution ratio due to the change of the pressure of the sample gas can be improved. Moreover, this invention can provide an air-fuel ratio measuring device with a simple construction and high reliability.

What is claimed is:

1. An air-fuel ratio measuring device for measuring an air-fuel ratio by measuring a residual component after air for dilution and sampled exhaust gas are mixed with each other, comprising:
   an exhaust gas suction line for sucking the exhaust gas;
   a dilution air suction line for sucking the dilution air, joining with the exhaust gas suction line;
   two capillary tubes branching from the exhaust gas suction line and the dilution air suction line on an upstream side of a joining position of the two lines;
   a mixture line extending from a joining point of the two capillary tubes and having a sensor for measuring the residual component, whereby the value of said residual component is used to calculate the air-fuel ratio; and
   a throttle nozzle provided on the exhaust gas suction line on an upstream side of a branch point of the capillary tube.

2. An air-fuel ratio measuring device according to claim 1, wherein the exhaust gas suction line and the dilution air suction line are joined at a surge tank to which a suction pump for forming negative pressure in the two lines is connected.

3. An air-fuel ratio measuring device according to claim 2, wherein a throttle nozzle is provided on the dilution air suction line on the upstream side of a branch point of a capillary tube and two respective branch points on the two lines are separated away from the surge tank for a predetermined distance.

4. An air-fuel ratio measuring device according to claim 1, wherein each of the two capillary tubes has a supplementary tube with a relatively large inner diameter and a main tube with an inner diameter which is sufficiently small as compared with that of the supplementary tube.

* * * * *